United States Patent [19]

Lambert et al.

[11] 4,238,477

[45] Dec. 9, 1980

[54] PROCESS OF PREPARING HOMOGENEOUS RESIN-POLYIODIDE DISINFECTANTS

[75] Inventors: Jack L. Lambert; Louis R. Fina, both of Manhattan, Kans.

[73] Assignee: Kansas State University Research Foundation, Manhattan, Kans.

[21] Appl. No.: 31,920

[22] Filed: Apr. 20, 1979

[51] Int. Cl.³ .................. A61L 2/16; C02F 1/42; C02F 1/50
[52] U.S. Cl. .................................. 424/79; 210/501
[58] Field of Search ............ 210/29, 62, 501, 24, 210/37 R, 60, 64; 424/79, 150; 422/37

[56] References Cited

U.S. PATENT DOCUMENTS

| | | |
|---|---|---|
| 3,316,173 | 4/1967 | Mills et al. ........................ 210/62 |
| 3,462,363 | 8/1969 | Mills ................................ 210/62 X |
| 3,817,860 | 6/1974 | Lambert et al. ............... 210/501 X |
| 3,923,665 | 12/1975 | Lambert et al. .................. 210/501 |
| 4,076,622 | 2/1978 | Costin ............................ 210/501 X |

Primary Examiner—Thomas G. Wyse
Attorney, Agent, or Firm—Tilton, Fallon, Lungmus & Chestnut

[57] ABSTRACT

Demand-type disinfectants are prepared from strong base anion exchange resin beads and elemental iodine. The resin is in the iodide form, and the iodine is applied with a water carrier which is recycled in contact with the resin and the stoichiometric amount of iodine to form the desired polyiodide (viz. $I_3^-$, $I_5^-$, or mixtures thereof). A homogeneous product of pre-determined polyiodide content is obtained.

14 Claims, 3 Drawing Figures

PLOT OF TIME VS. TEMPERATURE FOR THE PREPARATION OF $I_5^-$ RESIN DISINFECTANT FROM $I_3^-$ FORM

PROCESS OF PREPARING HOMOGENEOUS RESIN-POLYIODIDE DISINFECTANTS

BACKGROUND AND PRIOR ART

This invention relates to the preparation of demand-type broad-spectrum resin-polyiodide water disinfectants. Triiodide-quaternary ammonium resin disinfectants have heretofore received primary consideration, since when properly prepared, the iodine is tenaciously bound to the active sites of the resin and is released almost entirely on a demand-action basis. See Lambert and Fina U.S. Pat. Nos. 3,817,860 and 3,923,665. Also, see Fina, L. R. and Lambert, J. L. (1975), "A Broad-Spectrum Water Disinfectant that Releases Germicide on Demand," Second World Congress, International Water Resources Association, New Delhi, India, December 1975, Volume II, pp. 53-59.

Prior to the present invention, the preferred procedure for preparing the triiodide resins has been to form the triiodide ion in aqueous solution by dissolving iodine in a water solution of sodium or potassium iodide. The resulting solution containing the triodide ion is then applied to the resin, the triiodide ion exchanging with the anion of the resin as supplied by the manufacturer (usually chloride or sulfate). With this procedure, it has been found difficult to prepare resins containing only triiodide and in which all of the active sites of the resin have been converted to triiodide. After forming the resin, it has been necessary to wash it with water and/or with aqueous solutions of potassium iodide. There has been a need for a process where the desired form of the resin can be prepared directly on an exact stoichiometric basis.

It has been suggested that the resin could first be converted to the iodide, and then reacted with elemental iodine to form the triiodide. However, prior to the present invention, this procedure was not believed to be desirable for commercial purposes. As stated in U.S. Pat. No. 3,923,665 (col. 3, lines 62-69):

"In another procedure, the resin is first converted to the iodide ($I^{31}$) form by contacting it with a solution of potassium or sodium iodide, or other iodide salt, and a stirred aqueous slurry of the converted resin is contracted with elemental iodine. ($I_2$) to react with the absorbed $I^-$ to form bound $I_3^-$. This procedure is less desirable, since it is more difficult to assure precise saturation of the column with triiodide."

In applying elemental iodine to resin beads, the problem of iodine encrustation has been encountered. As the iodine is applied in aqueous solution, it tends to form a crust on the outside of the beads, comprising a deposit of $I_2$. Further, it has been difficult to obtain homogeneous products in which the iodine has been uniformly distributed throughout the resin beads being treated.

SUMMARY OF INVENTION

The process of the present invention can be used for preparing not only a triiodide resin disinfectant, but also disinfectants in which part or all of the active sites are in the form of higher polyiodides, such as penta-iodide ($I_5^-$). Using the known equivalent exchange capacity of the combining sites of the resin, the amount of iodine applied will be the exact stoichiometric amount to produce the $I_3^-$, $I_5^-$, $I_7^-$, or predetermined mixtures, such as a 50—50 mixture of triiodide and penta-iodide. The resin is first converted to the iodide form, and is thereafter contacted with a recycling stream of water which acts as a carrier for the iodine to be applied to the resin. The recycling stream also contacts a pre-measured amount of elemental iodine, which is gradually dissolved in the water. The contacting of the water solution of the iodine is preferably continued until all of the iodine has been absorbed from the water by the resin beads.

In the process of the present invention, only a very small proportion of the iodine being applied is dissolved in the water at any given time. This is due to the very limited solubility of $I_2$ in water. However, by using heated water to increase the solubility of the iodine, the process can be completed in a reasonable time. At the same time, the iodine is transferred to the resin so gradually and uniformly that a completely homogeneous product is obtained, and there is no tendency for the iodine to deposit on the outside of the beads as it is applied. On completion of the process, the disinfectant is ready for use. No further treatments except casual washing are required.

The resin beads may be contacted with the water carrier in a thin bed. For large scale commercial production, however, it is believed that the use of a fluidized bed will be desirable. In other words, the bed of resin beads being treated will be arranged and the flow rate of the water passing through the bed will be controlled to produce a fluidization of the bed in which the beads circulate freely within the bed, thereby further enhancing the uniformity of the contacting. However, as indicated, the process of this invention in its broad form can also be carried out with a static resin bed.

DRAWINGS

In the accompaning drawings.

DETAILED DESCRIPTION

Figure 1:
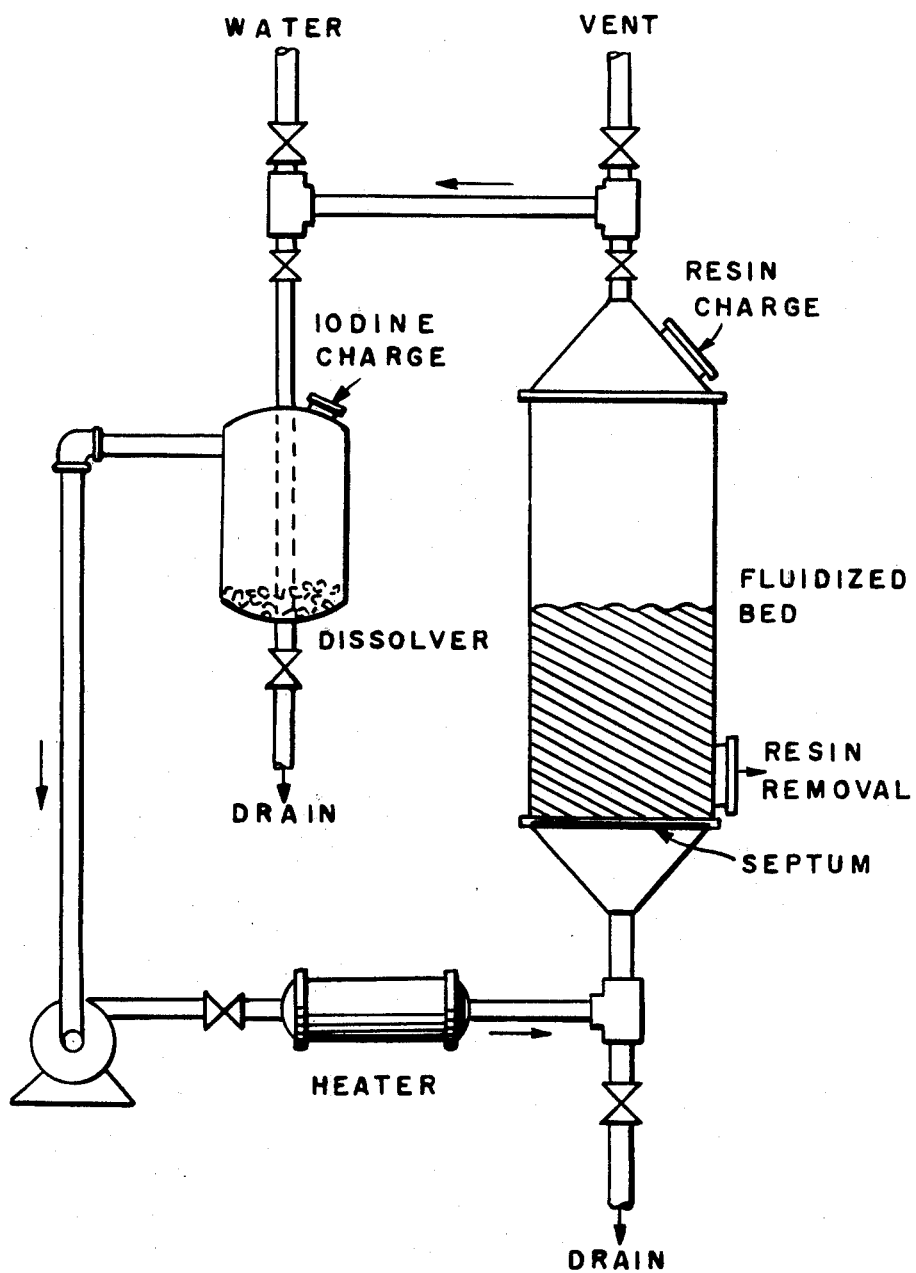
FIG. 1 illustrates commercial scale apparatus for practicing the method of this invention, including the using of a fluidized bed.

The present invention can be practiced with any strong base anion exchange resin, but quaternary ammonium anion exchangers are preferred, the term "strong base anion exchange resin" designates a class of resins either containing strongly basic (cationic) groups, such as quaternary ammonium groups, or which have strongly basic properties substantially equivalent to quaternary ammonium anion exchange resins. The classification of "strong base" resins contrasts with the "weak base" resins where the basic groups are amine nitrogen rather than quaternary ammonium groups.

In addition to the quaternary ammonium resins, which are commercially available from a number of companies, other strong base resins are known, such as the tertiary sulfonium resins, the quaternary phosphonium resins and the alkyl pyridinium resins. Commercially available quaternary ammonium anion exchange resins which can be used in practicing the present invention are identified in U.S. Pat. Nos. 3,817,860 and 3,923,665.

Although not required for practicing the present invention, commercial quaternary ammonium resins may be remethylated to assure that the active sites are in quaternary form. Some commercially available quaternary ammonium resins contain a small portion of tertiary amine sites. These can be eliminated by treatment of the commercial resin with methyliodide or dimethyl sulfate in ethyl alcohol solution. The resin can be allowed to react with the solution overnight, and the remaining solution drained off, and the resin washed with a sequence of ethanol and ion-free water. (See Example VIII of U.S. Pat. No. 3,817,860.) In practicing the present invention, the strong base anion exchange resin is first converted to the iodide ($I^-$) form. Of course, if the resin was already in the iodide form, such conversion would not need to be performed by the manufacturer of the disinfectant. However, most quaternary ammonium resins are supplied either as the chloride or sulfate.

To convert the resin to the iodide form, it is treated with a solution of potassium or other soluble iodide salt. Preferably, the solution should be free of other anions which would compete with the iodide ion for replacement of the chloride or sulfate in the resin. The amount of iodide required is calculated on a weight or volume basis from data supplied by the resin manufacturer; an excess of the iodide salt between 1.2 and 2.0 times the equivalent exchange capacity of the resin can be used to insure complete conversion to the iodide form. The converted resin is thoroughly washed in a column with ion-free water to a negative test with silver nitrate (essentially little trubidity of silver iodide).

To determine the amount of iodine required to prepare the desired polyiodide or mixture of polyiodides, the equivalent exchange capacity of the resin should be known. Usually, the exchange capacity of the resin is supplied by the manufacturer. However, if necessary, it can be readily determined, for example, by the procedure described in U.S. Pat. No. 3,817,860 (col. 9, lines 15-28).

The amount of iodine to be applied to the resin is then determined. For example, if the iodide is to be converted to triiodide, one equivalent of $I_2$ will be required for each equivalent of the resin, or two equivalents of $I_2$ for each equivalent of the resin for the penta iodide. For example, with 50 milliequivalents (meq) of Dowex-X8 resin (Dow Chemical Company, Midland, Michigan), 50 meq of $I_2$ would be required to prepare the stoichiometric triiodide.

Water is used as the carrier to apply the iodine gradually and uniformly to the resin. More specifically, the water is circulated in a recycling stream which is arranged to contact the iodine and the resin beads in sequence. The circulating water gradually dissolves the iodine and carries it as $I_2$ in solution to the resin beads. The water should be free of halide ions, and is preferably free of all other ions. For example, distilled or de-ionized water can be used. While the transfer can be carried out with the water at room temperature (20°-25° C.), it is preferable to heat the water so that it carries more iodine. Even at elevated temperatures, the solubility of iodine in water is very limited. For example, 0.03 grams of iodine dissolve in 100 cc of water at 25° C. At 50° C., the saturation solubility is increased to 0.078 grams per 100 cc. Preferably, therefore, the iodine is transferred by the water with the water being maintained at a non-boiling temperature of not lower than 40° C. A suitable temperature range for commercial use is from 60° to 95° C. At 70° C., for example, transfer may be completed in from 4 to 6 hours, while at 40° C., the completion of the transfer may require from 24 to 48 hours.

Where the resin is to be reacted with a pre-determined quantity of iodine, the transfer can be carried out to substantial exhaustion of the iodine. This is accomplished by continuing the circulation until all of the crystalline iodine has been dissolved and until the dissolved $I_2$ has all been absorbed by the resin beads. The completion can be determined by analyzing the circulating water for iodine, and finding that the iodine has dropped below detectable limits, such as by using the cadmium iodide-linear starch reagent described in Lambert, *Anal. Chem.*, 23, 1247 (1951), and Lambert and Rhodes, *Anal. Chem.*, 28, 1629 (1956). However, total exhaustion of the iodine in the water is not required, since any residual iodine in the water is a relatively small amount of that being applied. Therefore, substantial completion is sufficient for the purpose of the present invention.

FIG. 1 of the drawing provides a diagrammatic illustration of the method of this invention. The resin is converted to the iodide form, as described above, and the amount to be reacted is charged to the reactor through the indicated access port. It is distributed in a thin bed, as illustrated, over a microporous support plate. As shown, the reactor is in a circuit with a dissolver. The pre-determined amount of iodine crystals are introduced into the dissolver through the indicated charging port. Crystals may fall to the bottom of the dissolver, as indicated in the drawing. The circuit also contains a heater and a pump. Ion-free water is introduced into the circuit until it completely fills the reactor, dissolver, heater, pump and pipe lines. The pump is then operated continuously to provide a recycle-type circulation. The heater is controlled to provide the desired water temperature, such as 70°-80° C. Within the dissolver, the water becomes saturated with iodine. To promote the dissolving to full saturation, if required, an agitator may be employed within the dissolver, as shown. The saturated water solution of the iodine then flows through the reactor. Branch pipe lines may be provided beneath the microporous support plate, as indicated to assure uniformity of flow through the support plate and the resin bed. The circulating water exits through an outlet at the top of the reactor, and is returned through the pump and heater to the dissolver to pick up additional iodine. The circulation is continued until the iodine has been completely dissolved, and until substantially all of the iodine has been transferred to the resin beads. At that time, the water may be drained from the system, for example through the drain connection, as indicated. Reacted resin is then removed from the reactor, for example, through the indicated access port. The process is then repeated with a new batch of resin.

Where disinfectants are to be prepared containing higher polyiodides than the triiodide, the starting material may be resin in triiodide form. For example, where the triiodide resin has been previously prepared, an additional equivalent of iodine may be applied to form the penta-iodide. Usually, however, it will be more efficient to utilize resin in iodide form, and to carry the iodine transfer as far as required to prepare the desired final product. This way, polyiodide disinfectants, such as those containing substantially entirely $I_5^-$ or $I_7^-$, etc., can be readily prepared. Further, if desired, resin products may be prepared containing a mixture of polyiodides, such as a mixture of triiodide and penta-iodide.

EXAMPLE I

In a laboratory experiment, triiodide and/or penta-iodide disinfectant resins can be prepared by a procedure demonstrating the principle of the present invention.

A 350-ml. capacity, 90-mm i.d. fritted pyrex glass funnel is modified by removing the stem, cutting the side of the funnel so that it was approximately 60 mm overall height, and cutting 2 mm×20 mm segments approximately 4 mm apart around the circumference of the funnel. The modified funnel is then inverted, a mat of pyrex glass wool laid on top (previously bottom) of the fritted glass disc, and the whole inverted funnel placed in the crystallization dish which contains a small magnetic stirring bar.

A measured amount of iodine, $I_2$, is placed on the pyrex wool mat, and ion-free water is added to cover the inverted funnel. The amount of iodine is calculated from the equivalent exchange capacity of the resin to be used. A quaternary ammonium anion exchange resin is converted to the iodide ($I^-$) form by washing with a water solution of KI free of other ions. The iodide resin is added to the crystallizing dish outside the funnel, making a thin layer on the bottom. The crystallizing dish with funnel, is placed on a magnetic stirrer and the magnetic stirrer adjusted to moderate speed. A flat glass plate is placed over the crystallization dish to prevent evaporation and loss of iodine.

The stirring action thrusts the room temperature (25°-30° C.) water to the side and out through the slots cut in the side of the funnel. The water passes over the strong base resin, continues upward along the inside of the crystallizing dish, and down the center of the inverted funnel dissolving the solid iodine thereon. The iodine solution continues downward through the fritted glass disc of the funnel to the stirring bar, and the cycle repeats. The gentle pumping action maintains a flow of iodine solution over the strong base resin.

The triiodide-resin disinfectant prepared as described above can be used as a starting material for preparing a penta-iodide resin disinfectant. The procedure as described is repeated, using the triiodide-resin as the starting material, and applying a second equivalent of iodine, thereby preparing the penta-iodide disinfectant.

EXAMPLE II

Pentaiodide ($I_5^-$) resin was prepared from a commercial grade quaternary ammonium ion exchange resin (un-remethylated Dowex 1X8 resin, 50-100 mesh) in the chloride ($Cl^-$) form by first treating 100 milliequivalents (meq) of resin with excess potassium iodide solution, draining off the solution, repeating the treatment a second time, and again draining the resin. The resin was then washed thoroughly with distilled water.

Figure 2:
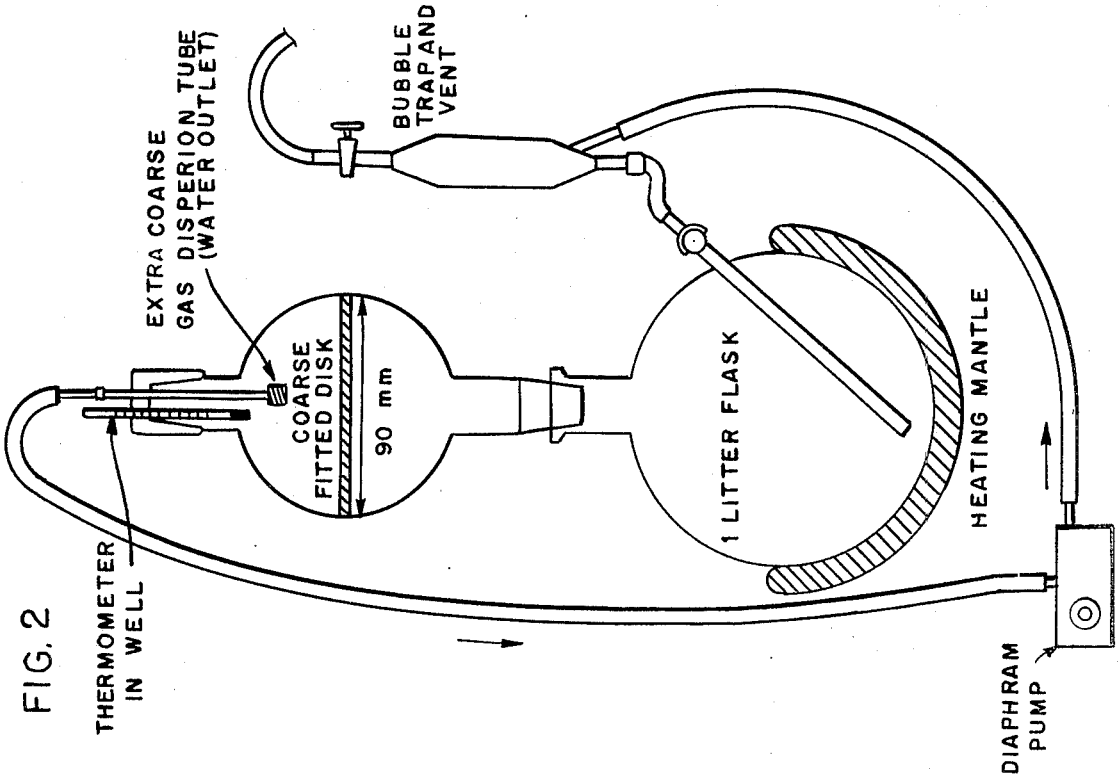
FIG. 2 illustrates laboratory scale apparatus.

This resin, now in the iodide ($I^-$) form, was charged to the upper bulb in the apparatus shown in FIG. 2, and 50.76 g. of iodine placed in the one liter flask. This amount of iodine constitutes twice the 100 meq exchange capacity of the resin. The entire apparatus was filled with water and the diaphragm pump started at a 7% dial reading. The flow rate at this setting was 125 ml per minute. At this rate of flow, the resin bed was gently fluidized. The temperature of the circulating water was maintained at 60° C. by the heating mantle shown. Air was vented from the trap when bubbles appeared. Circulation was continued for 14 hours. At the end of this time, the iodine had all disappeared and the color of the circulating water had faded to essentially clear.

At this point, the absorption of the iodide was complete. The heating mantle was turned off and the circulation continued until the temperature of the water had dropped to room temperature. The supernatant liquor was drained off and the $I_5^-$ resin product washed twice with distilled water.

EXAMPLE III

In commercial practice the process would be conducted in different equipment than the laboratory set-up of FIG. 2. For example, an apparatus like that illustrated in FIG. 1 could be used. The controls for measuring and maintaining the temperature and the flow rate are not shown in FIG. 1, since this could be done either manually or automatically. All materials in contact with iodine or iodide solutions should be protected from corrosion. Glass and teflon are two materials that resist attack by such solutions.

The first step is the conversion of the resin to the iodide form. The required amount of the resin to be treated is measured into the fluidized bed reactor. The exchange capacity of the resin is specified by the manufacturer, usually in equivalents per liter, or other unit of volume. A typical resin might have a capacity of about 1.4 gram equivalents per liter. If 100 liters (0.1 m³) of resin were to be used, the amount of KI required to convert this to the iodide form is then calculated as $$\frac{1.4 \times 100 \times 166.02 \times 1.5}{1000} = 34.86 \text{ kg,}$$

where the molecular weight of KI is 166.02, and 1.5 times the stoichiometric amount of KI is used to insure complete conversion. This is charged to the dissolver.

The system is then filled with water and the pump started. The flow rate through the resin bed is not critical at this point, so long as the resin beads are not washed out of the reactor. The bed of resin may remain in the packed state or may be fluidized. Temperatures in the range of 10° to 30° C. are satisfactory for this operation. Circulation should be continued until all of the water in the system has made four or more passes through the bed.

After all of the KI is dissolved and has been absorbed by the resin beads, the remaining water containing the excess KI and the ions removed from the resin by the exchange is drained to the sewer. The resin is then washed with water several times until the effluent is essentially free of iodideions.

The amount of iodine ($I_2$) needed to form the desired polyiodide is then charged to the dissolver. If pentaiodide is desired, this is calculated as $$\frac{1.4 \times 100 \times 2 \times 253.8}{1000} = 35.53 \text{ kg of } I_2,$$

where 253.8 is the molecular weight of elemental iodine ($I_2$). Alternatively, a mixed $I_3^-$-$I_5^-$ product can be prepared.

The system is filled with water and the pump started. The flow rate through the reactor is controlled between incipient fluidization as the lowest rate and complete wash out of the resin beads as the highest rate, the best operation being a rate about halfway between these two extremes. When the whole system is full of water and all air has been vented, the temperature of the circulating water is adjusted to a temperature between 50° and 70° C. where it is maintained. The higher the temperature, the more rapidly the iodine is dissolved and absorbed by the resin.

When the iodine has been completely absorbed by the resin, the color of the water will become lighter. This will take 8 to 24 hours, depending on the temperature used. The circulation of water can then be stopped and the water drained from the system. The resin should be washed by filling the system with fresh water, circulating it through the bed for a few minutes, and then draining the wash water to the sewer. The pentaiodide resin can then be removed from the reactor as a finished product.

EXAMPLE IV

Figure 3:
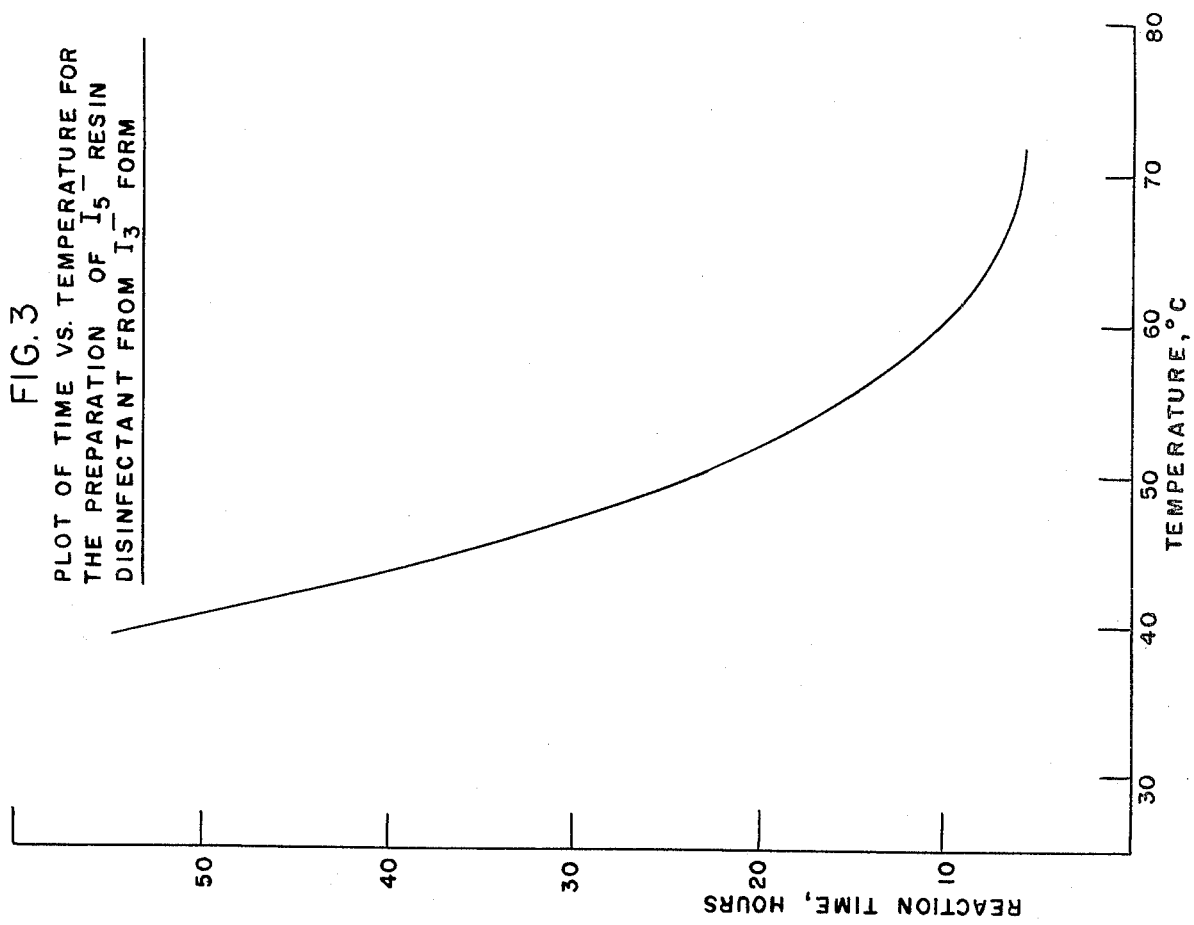
FIG. 3 is a graph representing the change in reaction time with temperature.

Utilizing a reaction procedure like that of Example II, additional experimental data was collected, as summarized below, in Table A and in the attached diagram of FIG. 3. The remethylation of the quaternary ammonium ion exchange resin (Dowex 1X8, Dow Chemical Company, Midland, Mich.) was carried out by the procedure described in our prior U.S. Pat. No. 3,923,665. As shown particularly by the graph of FIG. 3, the conversion of triiodide to pentaiodide is favored by increasing temperature, the most desirable temperature range being from about 60° to 70° C. Although the conversion can be carried to the $I_7^-$ stage, it is preferred to terminate the conversion at $I_5^-$, preparing $I_3^-$, $I_5^-$, or mixtures of $I_3^-$ and $I_5^-$. It has been found that the ion exchange beads are subject to decrepitation as the iodine content is increased from $I_5^-$ to $I_7^-$. However, the beads are stable at the $I_5^-$ stage.

TABLE A

| Reactions, resin forms[a] | Meq. of resin, initial form | Grams iodine added | Temp., °C. | Reaction time, hours | Residual iodine, ppm.[b] |
|---|---|---|---|---|---|
| $I^- \to I_3^-$ | 100 | 25.38 | 60.5 | 13.5 | 0[c] |
| $I_3^- \to I_5^-$ | 100 | 25.38 | 39.7 | 53.5 | 11.0 |
| $I_3^- \to I_5^-$ | 100 | 25.38 | 50 | 22.8 | 13.1 |
| $I_3^- \to I_5^-$ | 100 | 25.38 | 60.5 | 10 | 5.9 |
| $I_3^- \to I_5^-$ | 100 | 25.38 | 70 | 4.5 | 14.0 |
| $I_5^- \to I_7^-$ | 100 | 25.38 | 50 | 30.6 | 30.7[d] |
| $I_5^- \to I_7^-$ | 100 | 25.38 | 50 | 29.3 | 30.7[d] |

[a] strong base, quaternary ammonium ion exchange resin: Dowex 1 × 8, remethylated; initial form → final form.
[b] residual concentration of iodine in recirculated supernatant solution after cooling to room temperature, as determined by modified Black and Whittle colorimetric method.
[c] residual concentration below level of detection, which is approximately 0.1 ppm.
[d] residual iodine concentration of combined supernatant solutions of both $I_5^{31} \to I_7^{31}$ preparations.

We claim:

1. The process of preparing a homogeneous resin-polyiodide disinfectant containing a pre-determined quantity of a selected polyiodide or mixture of polyiodides, comprising:
   (a) converting strong base anion exchange resin beads to the iodide($I^-$) form, the equivalent exchange capacity of the combining sites of the resin being known, said iodide resin beads being contained in a reactor;
   (b) selecting the equivalent amount of crystalline iodine for reaction with the $I^-$ of the resin to produce the desired polyiodide disinfectant, said iodine being contained in a dissolver separate from said reactor;
   (c) circulating water in a recycling stream arranged to contact sequentially said iodine in said dissolver and said resin beads in said reactor, said circulating water gradually dissolving said iodine and carrying it as $I_2$ in a substantially saturated solution to said resin beads for absorption thereby, said water being free of halide ions; and
   (d) continuing said circulation until substantially all of said amount of crystalline iodine has been dissolved by said water and until substantially all of said $I_2$ has been absorbed by said resin beads.

2. The process of claim 1 in which said resin is a quaternary ammonium resin.

3. The process of claim 1 or claim 2 in which said water is maintained at a non-boiling temperature of not lower than 40° C.

4. The process of claim 1 or claim 2 in which said water is maintained at a temperature of from 60° to 95° C.

5. The process of claim 1 in which said equivalent of iodine is the amount required to convert all of the $I^-$ of said resin to triiodide ($I_3^-$).

6. The process of claim 1 or claim 2 in which the equivalent amount of said iodine is the amount required to convert all of the $I^-$ of said resin to penta-iodide ($I_5^-$).

7. The process of claim 1 in which said equivalent amount of iodine is the amount required to convert the $I^-$ of said resin to a mixture of triiodide ($I_3^-$) and penta-iodide ($I_5^-$).

8. The process of claim 1 in which said resin beads are contacted with said water in a bed of said beads which is fluidized by the flow of said water therethrough, said reactor being a fluidized bed reactor.

9. The process of preparing a homogeneous resin-triiodide disinfectant containing a pre-determined quantity of triiodide ($I_3^-$), comprising:
   (a) converting quaternary ammonium anion exchange resin beads to the iodide ($I^-$) form, the equivalent exchange capacity of the combining sites of the resin being known, said resin beads being contained in a reactor;
   (b) selecting the equivalent amount of crystalline iodine for reaction with the $I^-$ of the resin on a stoichiometric basis to convert the quaternary ammonium sites to triiodide, said iodine being contained in a dissolver separate from said reactor;
   (c) circulating water in recycling stream arranged to contact said iodine in said dissolver and said resin beads in said reactor, said circulating water gradually dissolving said iodine and carrying it as $I_2$ in a substantially saturated solution to said resin beads for absorption thereby, said water being maintained at a non-boiling temperature of not lower than 40° C. and being free of halide ions; and
   (d) continuing said circulation until substantially all of said amount of crystalline iodine has been dissolved by said water and until substantially all of said $I_2$ has been absorbed by said resin beads.

10. The process of claim 9 in which said resin beads are contacted with said water in a bed of said beads which is fluidized by the flow of said water therethrough, said reactor being a fluidized bed reactor.

11. The process of claim 9 or claim 10 in which said water is maintained at a temperature of from 60° to 95° C.

12. The process of preparing a homogeneous resin-penta-iodide disinfectant, comprising:
   (a) converting quaternary ammonium anion exchange resin beads to the iodide ($I^-$) form, the equivalent exchange capacity of the combining sites of the resin being known, said iodide resin beads being contained in a reactor;

(b) selecting the equivalent amount of crystalline iodine for reaction with the $I^-$ of the resin on a stoichiometric basis to produce the penta-iodide disinfectant, said iodine being contained in a dissolver separate from said reactor;

(c) circulating water in a recycling stream arranged to contact sequentially said iodine in said dissolver and said resin beads in said reactor, said circulating water gradually dissolving said iodine and carrying it as $I_2$ in a substantially saturated solution to said resin beads for absorption thereby, said water being maintained at a non-boiling temperature of not lower than 40° C. and being free of halide ions; and (d) continuing said circulation until substantially all of said amount of crystalline iodine has been dissolved by said water and until substantially all of said $I_2$ has been absorbed by said resin beads.

13. The process of claim 12 in which said resin beads are contacted with said water in a bed of said beads which is fluidized by the flow of said water therethrough, said reactor being a fluidized bed reactor.

14. The process of claim 12 in which said water is maintained at a temperature of from 60° to 95° C.

* * * * *